United States Patent [19]

Magnani et al.

[11] Patent Number: 5,753,221
[45] Date of Patent: May 19, 1998

[54] TRANSFORMED ERYTHROCYTES, PROCESS FOR PREPARING THE SAME, AND THEIR USE IN PHARMACEUTICAL COMPOSITIONS

[75] Inventors: Mauro Magnani; Luigia Rossi, both of Urbino, Italy

[73] Assignee: Communaute Economique Europeene, Luxembourg, Luxembourg

[21] Appl. No.: 146,060

[22] PCT Filed: Jun. 9, 1992

[86] PCT No.: PCT/EP92/01291

§ 371 Date: Nov. 3, 1993

§ 102(e) Date: Nov. 3, 1993

[87] PCT Pub. No.: WO92/22306

PCT Pub. Date: Dec. 23, 1992

[30] Foreign Application Priority Data

Jun. 14, 1991 [EP] European Pat. Off. ............. 91401602

[51] Int. Cl.$^6$ .............. A01N 43/04; C12N 5/06; G01N 31/00; G01N 33/48

[52] U.S. Cl. ............... 424/93.73; 424/9.321; 424/93.21; 424/179.1; 424/450; 435/240.21; 514/43; 514/45; 514/47; 514/49

[58] Field of Search ............... 514/44, 7, 43, 514/45, 47, 49; 424/93.1, 450, 93.21, 93.73, 9.321, 179.1; 435/240.1, 240.21, 240.26

[56] References Cited

FOREIGN PATENT DOCUMENTS 0101341 2/1984 European Pat. Off. .
0298280 1/1989 European Pat. Off. .
9105800 5/1990 WIPO .

OTHER PUBLICATIONS

European Search Report No. 91 40 1602.
Biochemical and Biophysical Research Communications 1989 V161(2):393–398.
Biochemical and Biophysical Research Communications 1989 164(1): 446–452.
Chemical Abstracts, 1989 111, p. 22, Abstract# 111:49973u.
Federation European Biochemical Societies (FEBS) 1984 247(1): 57–60.
Biochemstry, 1982, 21:3950–3955.
Proc. Natl Acad Sci, USA, 1987; 84: 7368–7372.
Proc. Natl Acad Sci USA, 1986 83:8333–8337.
Ropars et al. 1985. Biblthca haemat., 51:82–91.
Sprandel et al. 1981 J. Inhor. Metab. Dis. 4:99–100.
Hubbard et al., 1980. Biochemical Society Transactions 8(5):578.
Fanger et al., Chemical Abstracts, 1991, Abstract No. 115:64752X ; vol. 115, p. 99.

*Primary Examiner*—Brian R. Stanton
*Attorney, Agent, or Firm*—Bierman and Muserlian

[57] ABSTRACT

The invention relates to compositions of erythrocytes that have been modified following hypotonic lysis and resealing by addition of 2',3'-dideoxycytidine-5'-triphosphate (ddCTP) or 3'-azido-3'-deoxythymidine-5'-triphosphate (AZT-TP). These compositions may also contain ATP. Also disclosed are methods of preparing these compositions.

11 Claims, 3 Drawing Sheets

TRANSFORMED ERYTHROCYTES, PROCESS FOR PREPARING THE SAME, AND THEIR USE IN PHARMACEUTICAL COMPOSITIONS

BACKGROUND OF THE INVENTION

The invention relates to transformed erythrocytes, to a process for preparing the same and to their use in pharmaceutical compositions, more particularly in the field of the treatment of pathologies caused by the infections of a human or animal by RNA type viruses.

Among these pathologies, acquired immunodeficiency syndrome (AIDS) is a lethal multisystem disease that has become a major public health problem.

AIDS is caused by the human immunodeficiency virus (HIV), which replicate primarily within T cells and macrophages (monocytes) leading to a loss of $CD4^+$ cells and culminating in severe immunosuppression.

It is now clear that AIDS is no longer confined to homosexual men and intravenous drug users but is spread in the heterosexual population as well. Furthermore, pediatric AIDS is a growing problem.

Treatment of AIDS is based on the assumption that continued viral replication is involved in both the development and progression of the disease. The ability to grow the virus have made possible the identification of a class of compounds known as dideoxynucleosides that inhibit in vitro HIV replication and which are not new agents since studies on these compounds were initiated in the 1960' and 1970', before human retroviruses were discovered. Furthermore, these nucleoside analogs are well known as reagents for the Sanger DNA-sequencing procedure (Sanger F. et al., (1977). DNA sequencing with chain-terminating inhibitors. Proc. Natl. Acad. Sci. 74: 5463).

AZT (Zidovudine: 3'-azido-3'-deoxythymidine) was the first nucleoside analog to be tested clinically and found to reduce the morbidity and mortality associated with severe HIV infection. However, due to dose-limiting toxicity, particularly bone marrow suppression, other dideoxynucleosides were studied as potential therapeutic agents.

2',3'-Dideoxycytidine (ddCyd), unlike the naturally occurring 2'-deoxynucleoside, lacks the hydroxyl (—OH) group in the 3'-position of the sugar ring. ddCyd at concentrations equal to or higher than 0.5 μM completely protects target helper/inducer T cells against HIV infections and enables them to survive and grow. Under conditions of low multiplicity of infection, concentration equal to or higher than 10 nM of ddCyd can suppress the virus.

Furthermore, ddCyd is the most active as inhibitor of HIV replication in vitro among all the dideoxynucleoside analogs tested. ddCyd is also resistant to cytidine deaminase (a major catabolic enzyme for cytidine analogs), has good bioavailability, straight forward pharmacokinetic clearance by the kidney, failure to reduce normal intracellular pyrimidine pools and when clinically tested produced immunologic and virologic improvement in AIDS patients and a toxicity profile that does not overlap with that of AZT.

ddCyd, as other nucleoside analogs, exerts its antiviral effect by inhibiting the action of reverse transcriptase in the HIV life cycle. To do this, ddCyd must be phosphorylated to the 5'-triphosphate and this phosphorylation occurs by cellular and not viral kinases through its 5'-monophosphate derivative and then by CMP/dCMP kinase and kinase to the 5'-diphosphate and 5'-triphosphate respectively.

It has been demonstrated that dideoxynucleosides concentration that inhibit HIV replication are 10- to 20-fold lower than those that inhibit the proliferation and survival of host cells. DNA polymerase alpha, in fact, is relatively resistant to the effect of dideoxynucleosides while DNA pol gamma (the mitochondrial DNA pol) and DNA pol beta are much more susceptible to inhibition and this fact may account for some of the observed clinical toxicities.

In clinical trials investigating ddCyd, plasma levels of the drug during the infusion in patients receiving 0.09 mg/Kg exceeded the in vitro concentrations (more than 0.5 μM) that confer complete protection against a high multiplicity of viral infection in vitro. However, at four hours after intravenous administration of ddCyd at this level, the plasma level decreased to below 0.1 μM. The plasma half life of ddCyd was found to be 1.2 h and the cerebrospinal fluid/plasma ratio was 0.14 indicating that ddCyd partially penetrates the brain.

Significant dose-related toxicity associated with the administration of nucleoside analogs remains the limiting factor for their effective use in the treatment strategies. To evaluate the possibility of overcoming the short plasma half-life (approximately 1 h for AZT and ddCyd), and the slow cerebrospinal fluid penetration of these antiviral drugs new strategies for ddCyd administration including the synthesis of prodrugs of nucleoside analogs have been investigated.

ddCMP(2',3'-dideoxycytidine-5'-phosphate) has been synthesized as a prodrug, encapsulated in human erythrocytes and it has been found that it is dephosphorylated by endogenous pyrimidine nucleotidases and subsequently released by the cells as ddCyd (Magnani M. et al., (1989). Human red blood cells as bioreactors for the release of 2',3'-dideoxycytidine, an inhibitor of HIV infectivity. Biochem. Biophys. Res. Commun. 164: 446–452).

This method allows the progressive release of ddCyd in the blood, thus increasing the half life of said ddCyd in the organism.

However, such a method is a solution neither to the problem of toxicity of ddCyd in the blood, nor to the obstacle constituted by phosphorylation which is needed for ddCyd to be active on the reverse transcriptase of virus.

HIV has been demonstrated in cells of the monocytes/macrophages (monocytes/macrophages) lineage in HIV seropositive individuals (Gartner S. et al., (1986). The role of mononuclear phagocytes in HTLV-III/LAV infection. Science 233: 215–219. Ho D. D. et al., (1986). Infection of monocyte/macrophages by human T lymphotropic virus type III. J. Clin. Invest. 77: 1712–1715). These cells are present in blood, lung, brain lymph node and skin. Infection of monocytes/macrophages does not result in the cytopathic effect found in HIV infected T lymphocytes and is associated with pneumonitis, dementia, neuropathy, dermatitis, etc. Thus, cells of the monocytes/macrophages lineage may serve as the reservoir for HIV in the infected host and may play a key role in the dissemination of the virus and pathogenesis of AIDS (Yarchoan R. and al., "Immunology of HIV Infection", Fundamental Immunology, Second Edition, 1989, pp. 1059–1073).

However, macrophages seem not to be very reactive with respect to antiviral drugs and the balance between the toxicity threshold of antiviral drugs and the active dose required is difficult to control.

One of the aims of the present invention is precisely to avoid the problem of toxicity of non-naturally occurring phosphorylated compounds susceptible of being active against pathogenic microorganisms, particularly retroviruses, and to allow the administration directly of said compounds under their active form, i.e. under their phosphorylated form.

Surprisingly, the present invention provides pharmaceutical compositions, the active substance of which specifically targets cells which in human or animal organisms are susceptible to be infected by pathogenic microorganism, such as lymphocytes, monocytes or macrophages above-mentioned, this enabling the administration of variable amounts of active substance and at frequencies which are appropriate for the pathology.

SUMMARY OF THE INVENTION

The invention relates to compositions comprising transformed erythrocytes containing phosphorylated compounds, which do not naturally occur in a human or animal organism, said compounds having the properties of:

inhibiting the reverse transcriptase, and being stable in erythrocytes.

The expression "phosphorylated compounds" corresponds to compounds comprising at least one phosphate group and, more particularly, to compounds comprising one, two, three phosphate groups. These are advantageously non naturally occurring nucleosides.

Advantageous nucleosides are those modified in the 2' and 3' positions, or in the 2' and 5' positions, advantageously 2',3'-dideoxy-purine nucleosides, or 2',3'-dideoxypyrimidine nucleosides or nucleosides comprising fluorine, i.e. in the 2' or 5' positions.

The expression "being stable in erythrocytes" means that the phosphorylated compounds which are involved in the compositions of the invention remain phosphorylated, and that no degradation products are derived from said phosphorylated compounds.

A test to check the stability of phosphorylated compounds in erythrocytes can be the following.

Heparinized human blood is washed twice in 10 mM HEPES, 140 mM NaCl, 5 mM glucose, pH 7.4 (Buffer A) to remove white blood cells and platelets and resuspended at 70% hematocrit in buffer A. These cells are dialyzed for 45 min using a tube with MW cut off 12–14 KDa against 50 volumes of 10 mM $NaH_2PO_4$, 10 mM $NaHCO_3$, 20 mM glucose, 4 mM $MgCl_2$, pH 7.4 containing 3 mM reduced glutathione and 2 mM ATP (Buffer B). The osmolarity of Buffer B is 58 m Osm. After this dialysis time osmolarity of the erythrocytes suspension ranged between 110–130 m Osm. After this time 16 µmoles of phosphorylated compound are added to each ml of erythrocytes suspension that is further dialyzed against 5 to 10 volumes of 16 mM $NaH_2PO_4$, pH 7.4, containing 4 mM phosphorylated compound (Buffer C) for a further 45 min. All these procedures are performed at 4° C.

Resealing of the erythrocytes is obtained by adding 0.1 volume of 5 mM adenine, 100 mM inosine, 2 mM ATP, 100 mM glucose, 100 mM Na-pyruvate, 4 mM $MgCl_2$, 0.194M NaCl, 1.606M KCl, 35 mM $NaH_2PO_4$, pH 7.4 per volume of dialyzed erythrocytes and incubated at 37° C. for 20 min. Resealed cells are then washed three times in buffer A and incubated at 6% hematocrit in 0.9% (w/v) NaCl containing 10 mM glucose, 5 mM sodium, potassium phosphate buffer, pH 7.4. At different time intervals (0 to 3 h) aliquots (200 µl) of the incubation suspensions are extracted with 100 µl 10% (w/v) $HClO_4$, centrifuged, neutralized and submitted to HPLC analyses to detect eventual metabolic product of the phosphorylated compound.

A phosphorylated compound is considered stable when after 1 h at 37° C. in a test as above is still present at a concentration not lower than 80% of its initial concentration.

A test to check the stability of a specific compound ddCTP in erythrocytes will be given hereafter.

The above-mentioned properties are valid in vitro, as well as in vivo.

More particularly, the invention concerns compositions characterized in that said phosphorylated compounds have the property of:

being integrated (i.e. transferred) from the erythrocytes to target cells, after integration of said phosphorylated compounds by the above said cells, remaining stable during a period of time sufficient for the inhibiting activity of the phosphorylated compounds on the reverse transcriptase with respect of RNA of the pathogenic microorganisms which have possibly contaminated said cells.

A test to check that there is integration (i.e. transfer) of the phosphorylated compounds to the above-mentioned cells can be the following.

Human erythrocytes containing the phosphorylated compound labeled with $^3H$ or $^{14}C$ on the nucleobase and processed to increase the number of IgG bound on their membrane are incubated with adherent monocytes/macrophages cells at a ratio of 100 erythrocytes per monocytes/macrophages for 3 h.

After monocytes/macrophages-erythrocytes incubation the dishes are extensively washed with RPMI 1640 medium to remove all erythrocytes not phagocytosed, followed by a 0.9% ammonium chloride washing step to remove adherent erythrocytes that are not yet phagocytosed.

Finally monocytes/macrophages after the phagocytosis step are extracted with 10% $HClO_4$ and processed as above for the HPLC separation of nucleotide and nucleotide analogs followed by liquid scintillation counting of the fractions collected at the exit of the HPLC system. The concentration of phosphorylated compound in monocytes/macrophages is determined by liquid scintillation counting of the fractions corresponding to the retention time in HPLC of the phosphorylated compound. The concentration of said phosphorylated compound must be the same or higher than that known to inhibit in vitro 50% of HIV reverse transcriptase activity.

A test to check that the phosphorylated compounds remain stable during a period of time sufficient for the inhibiting activity of said phosphorylated compounds on the reverse transcriptase can be the following.

Monocytes/macrophages are prepared from mononuclear peripheral blood cells obtained by centrifugation on Lymphoprep commercialized by Nyegaard & Co., Oslo, Norway. Adhesion is obtained in the presence of 20% heat inactivated human serum, while monocytes/macrophages (more than 95% pure) are infected by HIV-1 for 8 h at a p24 concentration of 40 ng/$10^7$ monocytes/macrophages cells. Mononuclear cells are then washed and further incubated with phosphorylated compounds loaded erythrocytes (1 µmol phosphorylated compound/ml erythrocytes) for 20 h. The non ingested red blood cells are then removed and monocytes/macrophages maintained in RPMI 1640 medium containing 10% FCS for 21 days. The amount of p24 in the medium are assayed. A phosphorylated compound is considered to be stable if the amount of p24 in the medium of $10^6$ cells after 21 days is less than 0.4 ng.

Advantageously, the phosphorylated compounds of the invention:

remain stable in erythrocytes during the target by the erythrocytes of cells, which cells are liable to integrate said phosphorylated compounds, remain stable during the integration of said compounds into said cells.

The above-mentioned conditions are valid in vivo, as well as in vitro.

The cells above-mentioned are those of the immune system of a human or animal organism, such as monocytes, macrophages, or lymphocytes.

The compositions of the present invention are more particularly characterized in that said phosphorylated compounds remain stable in said cells, at least about 3 hours after integration of said phosphorylated compounds (via the erythrocytes) into said cells for instance under the following in vitro conditions: RPMI 1640 medium containing 10% FCS, 5% $CO_2$, at 37° C.

The compositions of the invention are also characterized in that the phosphorylated compounds are triphosphorylated compounds and in that said transformed erythrocytes comprise no more than about 20% of degradation products, i.e. mono or diphosphorylated compounds originating from triphosphorylated compounds, about 10 days after the incorporation of said triphosphorylated compounds into the erythrocytes and when said erythrocytes are conserved for instance in the following conditions: CPDA-1 medium (commercialized by BIOTEST PHARMA, Dreieich, FRG) at +4° C.

In a preferred embodiment, the above-mentioned phosphorylated compounds are in the form of triphosphorylated compounds chosen from among:

2',3'-dideoxycytidine-5'-triphosphate (ddCTP), and/or

2',3'-dideoxyinosine-5'-triphosphate (ddITP), and/or

3'-azido-3'-deoxythymidine-5'-triphosphate (AZT-TP), and/or

2',3'-dideoxyfluorocytidine-5'-triphosphate, and/or

3'-azido-2',3'-dideoxy-5'-triphosphate, and/or

2',3'-didehydro-3'-deoxythymidine-5'-triphosphate, and/or

3'-azido-2',3'-dideoxyuridine-triphosphate, and/or

2'-deoxy-3'-thiacytidine-triphosphate, and/or 5-fluoro-2',3'-dideoxycytidine-triphosphate, and/or 2',3'-dideoxyguanosine-triphosphate, and/or 2',3'-didehydro-3'-deoxythymidine-triphosphate, and/or 2-amino-6-fluoro-2',3'-dideoxyinosine-triphosphate, and/or 9-(2,3-dideoxy-2-fluoro-b-D-threopentofuranosyl)-hypoxanthine-triphosphate.

Triphosphorylated compounds become diphosphorylated when ATP concentration in erythrocytes fall down to values of less than 1 mM (the normal concentration of ATP in erythrocytes being approximately 1.2 mM, and 1.6 mM in the loaded red blood cells of the invention).

To avoid the problem of abnormal low concentration of ATP in the red blood cells (erythrocytes), which can occur in some pathologies, such as those related to genetic enzyme defects, it can be appropriate to add ATP. Consequently, the invention also relates to compositions characterized in that said erythrocytes contain also ATP incorporated thereto.

In a preferred embodiment, the amount of ATP incorporated to said erythrocytes is such that the final concentration of ATP in erythrocytes is situated from about 1 to about 3 mM, advantageously from about 1.5 to about 2.5 mM.

The invention concerns also compositions such as described above, wherein the surface of erythrocytes is bound to molecules susceptible of being specifically recognized by the cells of the organism in which the phosphorylated compounds of the erythrocytes are to be integrated.

More particularly, the compositions of the invention are characterized in that surface proteins of the erythrocytes and/or transmembrane proteins of the erythrocytes, with said proteins being susceptible to be recognized by antibodies themselves susceptible to be recognized by cells of an human or animal organism, are in a reversible or irreversible clustered state, preferably in an irreversible state due to a covalent linkage with a cross-linking agent such as bis(sulfosuccinimidyl)suberate ($BS^3$).

The reversible clustered state is obtained by incubation of erythrocytes with $ZnCl_2$ according to a known process.

The invention also concerns compositions such as described above wherein said clustered proteins covalently cross-linked, are bound to said antibodies.

Binding of antibodies to erythrocytes mediate adherence of the erythrocytes to phagocytes, which subsequently engulf the red cell.

The adherence occur through the macrophage receptors for IgG (the Fc Receptor). Deposition of complement (in the form of C3b) on target erythrocytes increase further the immune adherence of the erythrocytes to the macrophage by activation of a further macrophage receptor specific for C3b (the CR1 receptor).

The compositions of the invention are efficient for the treatment of virus infections such as AIDS disease.

The invention also relates to pharmaceutical compositions comprising transformed erythrocytes, such as above described, associated with a physiologically acceptable carrier.

The pharmaceutical compositions are more particularly characterized in that the amount of erythrocytes is approximately of about 1 to about 10 ml, preferably of about 2 to about 5 ml, and the total amount of phosphorylated compounds is of about 1 to about 10 mM.

Preferably, the pharmaceutical compositions are in a suitable form for intravenous or intraperitoneal administration.

For this purpose, the compositions of the invention can be presented either under the form of sterile, sterilisable solutions, or under the form of injectable solutions, or under an appropriate form to be used for the extemporaneous preparation of injectable solutions. These solutions can be presented under the form of physiological aqueous solutions, particularly isotonic solutions, such as saline or glucose isotonic solutions.

In the pharmaceutical presentations for the parenteral administration the dose of the product to be administered is comprised from about 1 to about 100 µg, preferably from about 5 to about 50 µg, per kilogram of weight of patient.

For instance, 2 ml of compositions of the invention, such as erythrocytes containing ddCTP (ddCTP-loaded erythrocytes), can be administered every 10 days, 1 µl of composition containing $4.5 \times 10^6$ erythrocytes, with a ddCTP concentration of about 1 mM to about 10 mM.

The frequency of the injection containing the above-mentioned amount of active substances is of one per day to about one every 15 days.

The frequency of the compositions of the invention can be selected to allow some loaded erythrocytes to be always present in circulation. This means that the total amount of phosphorylated compound administered will increase, increasing the frequency of administration. However, loaded erythrocytes can also be prepared with more or less phosphorylated compounds (1 to 10 mM) so that both parameters (rate of phosphorylated compounds taken up by macrophages ingesting phosphorylated compounds loaded erythrocytes and concentration of phosphorylated compounds taken up per day) can be modified independently increasing the rate of phagocytosis or the content of phosphorylated compounds in the erythrocytes.

The invention also relates to a composition comprising transformed erythrocytes containing phosphorylated compounds, which do not naturally occur in a human or animal organism, said compounds having the properties of:

inhibiting the reverse transcriptase, and being stable in erythrocytes, and a substance active on lymphocytes as a combined preparation for simultaneous, separate or sequential use in antiviral therapy.

The invention also relates to any composition of the invention above described and a substance active on lymphocytes as a combined preparation for simultaneous, separate or sequential use in antiviral therapy.

The invention also relates to a composition comprising erythrocytes which contain ddCTP and a substance active on lymphocytes as a combined preparation for simultaneous, separate or sequential use in antiviral therapy.

The invention also relates to processes for preparing the compositions of the invention.

Such processes can be carried out according to the U.S. Pat. No. 4,931,276.

As for example, a process for preparing the compositions of the invention comprises the following steps:

lysing the membranes of the erythrocytes by dialysis of an aqueous solution of erythrocytes against an aqueous solution which is hypotonic with respect to the erythrocyte suspension, placing into contact the erythrocyte lysate with at least one of the phosphorylated compounds such as described above, and if necessary with ATP, increasing the osmotic pressure of the erythrocyte lysate mixed with the phosphorylated compounds with a solution which is hypertonic with respect to said lysate in order to reseal the membranes of the erythrocytes, washing the resealed cells.

In the process for preparing the composition of the invention, the erythrocytes can be either under the oxygenated form or under the deoxygenated form, but are advantageously in the oxygenated form.

In order to obtain transformed erythrocytes wherein surface and/or transmembrane proteins are clustered such as described above, the process above described can comprise the following steps:

treating the erythrocytes with a clustering agent of surface or transmembrane proteins, such as $ZnCl_2$, covalently linking the clustered proteins with a cross linking agent such as bis(sulfosuccinimidyl)-suberate ($BS^3$), with these steps being carried out, prior or after carrying out the process described above.

Preferably, these two steps for clustering the surface and/or transmembrane proteins are carried out after encapsulation.

of a control mouse (A), of an infected mouse (C) and of an infected mouse receiving ddCTP-loaded erythrocytes (B).

Figure 2A:
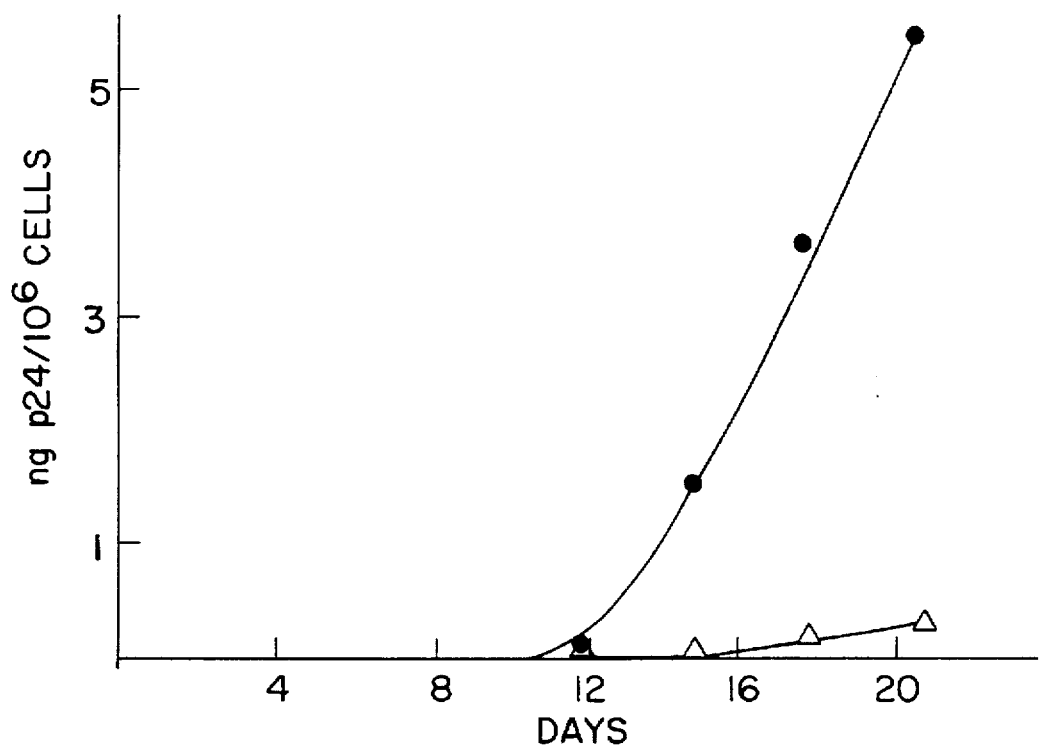

FIG. 2a represents the cellular p24 amount (expressed in ng of p24 in $10^6$ cells), plotted against the days in human monocytes/macrophages infected with HIV I (curve with black circles), and in human monocytes/macrophages infected with HIV I with added ddCTP-loaded erythrocytes (hollow triangles).

Figure 2B:
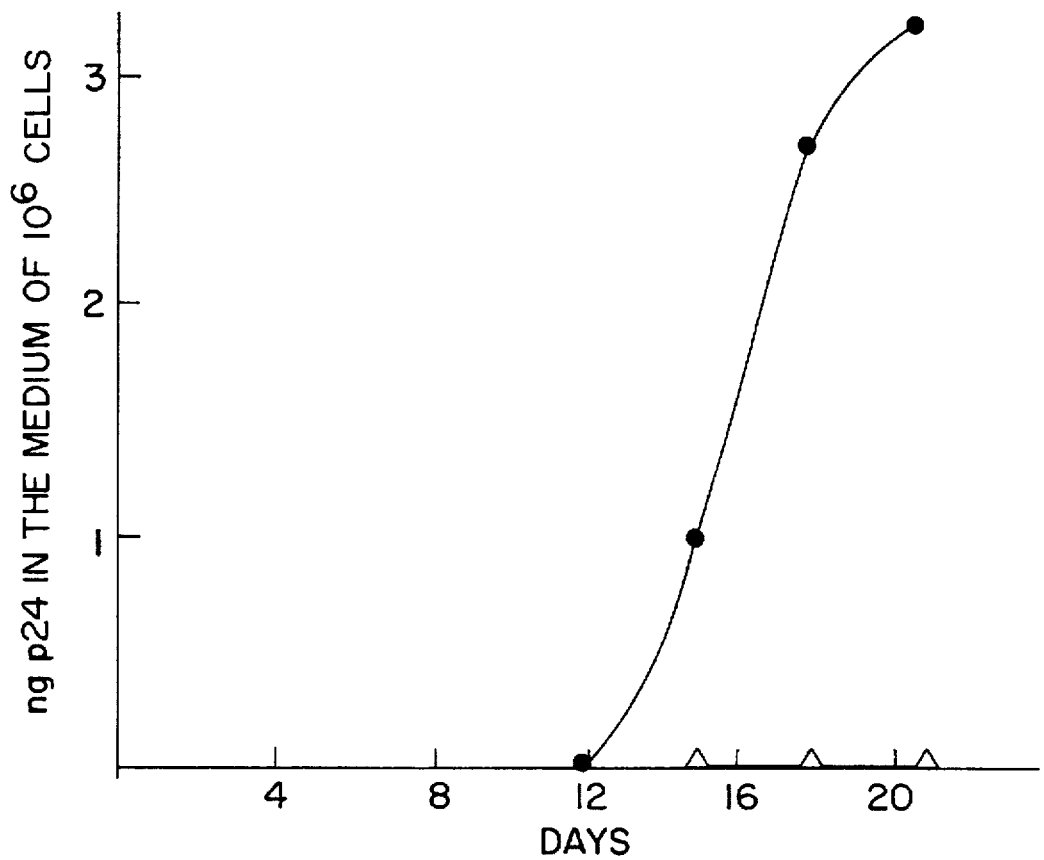

FIG. 2b represents the amount of p24 in the medium (expressed in ng of 24 in the medium of $10^6$ cells) plotted against the days in human monocytes/macrophages infected with HIV I (curve with black circles), and in human monocytes/macrophages infected with HIV I with added ddCTP-loaded erythrocytes (hollow triangles).

Figure 2C:
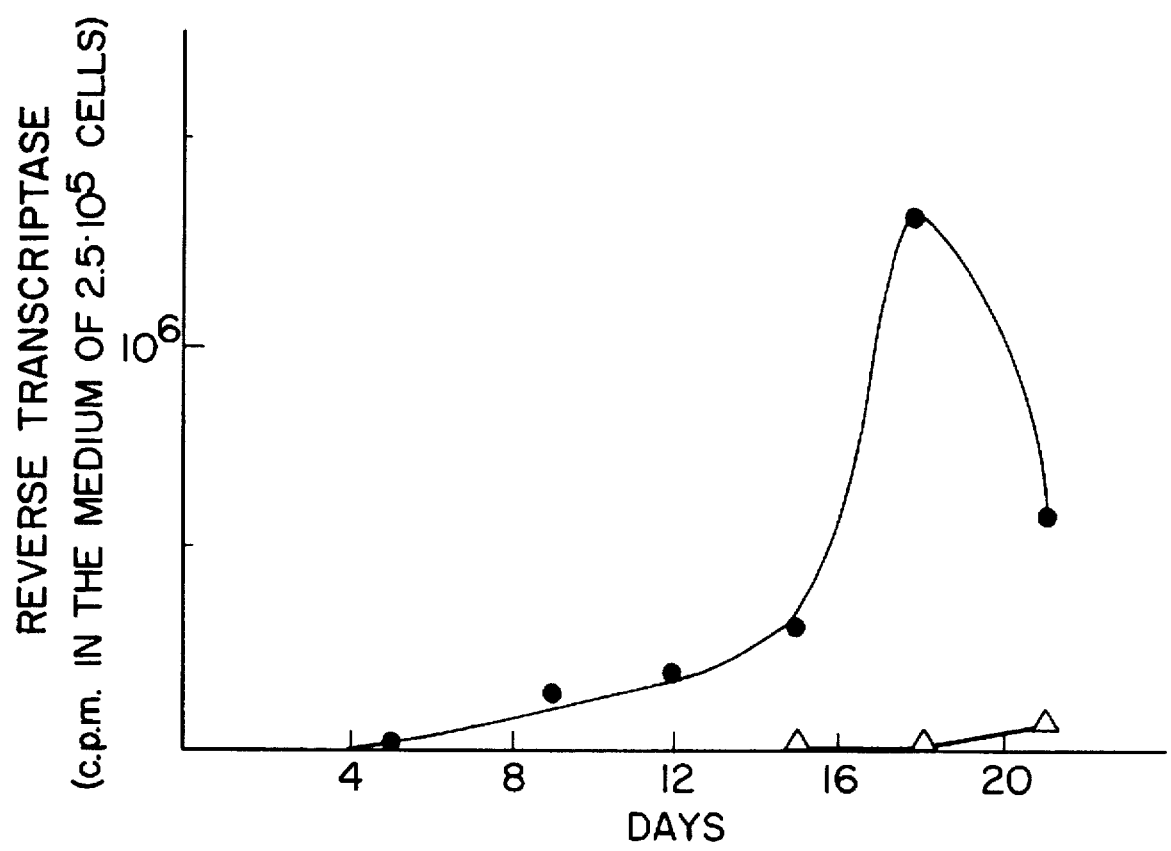

FIG. 2c represents the reverse transcriptase (expressed in c.p.m. in the medium of $2.5 \times 10^5$ cells) plotted against the days in human monocytes/macrophages infected with HIV I (curve with black circles), and in human monocytes/macrophages infected with HIV I with· added ddCTP-loaded erythrocytes (hollow triangles).

The invention will be more particularly illustrated by the following detailed description.

DETAILED DESCRIPTION 1) 2',3'-dideoxycytidine triphosphate encapsulation in erythrocytes:

Human and murine erythrocytes were used.

Heparinized blood was washed twice in 10 mM HEPES, 140 mM NaCl, 5 mM glucose, pH 7.4 (Buffer A) to remove white blood cells and platelets and resuspended at 70% hematocrit in buffer A. These cells were dialyzed for 45 min using a tube with MW cut off 12–14 KDa against 50 volumes of 10 mM $NaH_2PO_4$, 10 mM $NaHCO_3$, 20 mM Glucose, 4 mM $MgCl_2$, pH 7.4 containing 3 mM reduced glutathione and 2 mM ATP (Buffer B). The osmolarity of Buffer B was 58 m Osm. After this dialysis time the osmolarity of the erythrocytes suspension ranged between 110–130 m Osm. After this time 16 µmoles of ddCTP (Li salt) were added to each ml of erythrocytes suspension that was further dialyzed against 5 to 10 volumes of 16 mM $NaH_2PO_4$, pH 7.4, containing 4 mM ddCTP (Buffer C) for a further 45 min. All these procedures were performed at 4° C. Buffer C can be used three to four times.

Resealing of the erythrocytes was obtained by adding 0.1 volume of 5 mM adenine, 100 mM inosine, 2 mM ATP, 100 mM glucose, 100 mM Na-pyruvate, 4 mM $MgCl_2$, 0.194M NaCl, 1.606M KCl, 35 mM $NaH_2PO_4$, pH 7.4 per volume of dialyzed erythrocytes and incubated at 37° C. for 20 min. Resealed cells were then washed three times in buffer A and used as they were or further processed for the increase of their recognition by macrophages.

Human erythrocytes were loaded with 2',3'-dideoxycytidine triphosphate (ddCTP) to a final concentration of 1 mM. This encapsulation procedure is reproducible and can be modified to further increase the cellular concentration of ddCTP. Such modification can consist, during the dialysis steps, of adding various amounts of ddCTP.

2) Some properties of ddCTP-loaded erythrocytes:

Human erythrocytes submitted to the procedure described above are slightly microcytic 73±1.5 femtoliters (normal value 88±3.5 fl) and contain 27.5±2 g hemoglobin/100 ml cells (normal value 29.5±2.5). These cells have normal glycolytic rates (3 µmol of lactate/h/ml erythrocytes) and normal ATP concentrations (1.2 mM).

3) ddCTP stability in human erythrocytes:

The stability of ddCTP was evaluated both in human erythrocytes lysates as well as in intact erythrocytes.

Human erythrocytes lysates were prepared by adding 2 volumes of 3 mM sodium potassium phosphate buffer, pH 7.4, containing 3 mM mercaptoethanol, 0.5 mM EDTA to each volume of washed and packed erythrocytes. After 30 min at 4° C., the lysates were centrifuged for 1 h at 12,000×g to remove the cell membranes. The supernatants were then dialyzed overnight against 160 volumes of 0.9% (w/v) NaCl containing 10 mM Tris-HCl, pH 7.5, 10 mM $MgCl_2$ and 0.02 mM EDTA. The dialyzed lysates were then used for the studies of ddCTP stability. Briefly, 900 µl of lysate containing ddCTP 50 µM, 100 µM, 300 µM, 1.2 mM or 1.5 mM in a final volume of 1.2 ml were incubated at 37° C. At time intervals of 0, 15, 30 and 60 min, 250 µl of the incubation mixtures were removed and extracted with 125 µl of 10% (v/v) $HClO_4$. The perchloric acid extract was then neutralized with 23 µl of a 3M solution of $K_2CO_3$, diluted with 60 µl of 0.1M sodium potassium phosphate buffer pH 6.5, centrifuged 10 min at 10,000 rpm in an Eppendorf microcentrifuge and 100 µl of extract analyzed by HPLC as described below. The HPLC system used for the determination of ddCTP provides at the same time the possibility to measure ddCyd, ddCMP and ddCDP, appearing as metabolic products, was from Varian (Palo Alto, Calif., U.S.A.) and consisted of two Model 2010 pumps, a Model 2020 solvent programmer and a Model 2050 variable-wavelength detector. Integration of peak areas was obtained by means of an HP 3390A electronic integrator (Hewlett-Packard, Avondale, Pa., U.S.A.). A 5 µm Supelcosil LC-18 column (250 mm×4.6 mm I.D., Supelco, Bellefonte, Pa., U.S.A.) protected by a guard column (Pelliguard LC-18, 20 mm×4.6 mm I.D., pellicular packing material, 40 µm particles) was used throughout these studies. The mobile phase used for the separation of ddCTP and the other possible metabolic products (ddCyd, ddCMP and ddCDP) consisted of two eluents: a 0.1M $KH_2PO_4$ solution (pH 6.0) (buffer A) and a 0.1M $KH_2PO_4$ solution (pH 6.0) containing 10% (v/v) of methanol (buffer B). All buffer solutions, as well as standards and sample solutions, were filtered through a 0.22 µm membrane filter (Millipore).

The elution conditions used to obtain the chromatograms were: 2 min 100% buffer A, 4 min up to 10% buffer B, 4 min up to 40% buffer B, 3 min up to 100% buffer B and the same conditions are maintained for 7 min. The gradient was then returned to 100% buffer A in 2 min and the initial conditions restored in 8 min. The flow-rate was 1.3 ml/min and the detection wavelength was 272 nm. The analyses were performed at room temperature. Quantitative measurements were carried out by injection of standard solutions of known concentration. The molar absorption value used for standard calibration of ddCyd, ddCMP (2',3'-dideoxy-cytidine monophosphate), ddCDP (2'3'-dideoxy-cytidine diphosphate) and ddCTP at 272 nm was 9.1. The retention time for ddCTP was 3 min, for ddCDP 3.5 min, for ddCMP 6 min and 20 min for ddCyd.

Human erythrocytes lysates were found to be able to dephosphorylate ddCTP to ddCDP with a Vmax of 3±0.5 nmol/min/g HB and with a Km of 140 µM; ddCDP is then slowly converted to ddCyd.

Even long-term incubation provided only traces of ddCMP. In other words an enzymatic activity able to dephosphorylate ddCTP to ddCDP is present, although at low-levels, in human erythrocyte lysate. If ddCDP is further dephosphorylated to ddCMP, this is then converted to ddCyd by a red cell deoxypyrimidine nucleotidase.

ATP inhibition of ddCTP dephosphorylation was studied as above except that ATP 0, 1, 2, 4 mM was added to the incubation mixtures containing 100 µM ddCTP.

ATP, that is normally present in the erythrocyte at millimolar levels, is able to efficiently inhibit the ddCTP dephosphorylation. 2 mM ATP completely abolishes the dephosphorylation of ddCTP at 37° C.

2,3-Bisphosphoglycerate, even at 6 mM, does not affect ddCTP dephosphorylation rates.

ddCTP-dephosphorylation is also very pH-dependent with a maximum dephosphorylation rate at pH 8.4 and a value of 50% of this rate at pH 7.2 (the physiological value).

Under similar conditions 2',3'-dideoxyadenosine-5'-triphosphate (ddATP), 2',3'-dideoxyguanosine-5'-triphosphate (ddGTP) and 2',3'-dideoxyinosine-5'-triphosphate (ddITP) added to the erythrocyte lysate were stable both in the presence or absence of ATP for at least 2 h at 37° C.

The stability of ddCTP was then studied in ddCTP-loaded erythrocytes. In the intact cells ddCTP is stable even at 37° C. Extending the incubation time over 3 h a 20% decay of ddCTP was observed. This was concomitant to a decrease of 30% of cellular ATP.

In this case the stability of ddCTP (1 mM) in loaded erythrocytes was evaluated at 37° C. by incubation of ddCTP-loaded erythrocytes at 6% hematocrit in 0.9% (w/v) NaCl containing 10 mM glucose, 5 mM sodium, potassium phosphate buffer, pH 7.4. At different time intervals (0 to 5 h) aliquots (200 µl) of the incubation suspensions were extracted with 100 µl 10% (w/v) $HClO_4$, centrifuged, neutralized and submitted to HPLC analyses as above. In some experiments $^3$H-ddCTP (4 Ci/mmol, Moravek Biochemicals, Inc. Brea Ca) was used.

In this case fractions of 0.3 ml were collected at the exit of the wavelength detector of the HPLC system by using an LKB fraction collector and counted in a Packard liquid scintillation Counter. Both methods (HPLC detection and liquid scintillation counting) provided similar results (i.e. ddCTP was stable in erythrocytes until ATP was maintained at physiological concentrations of 1.2 mM, while ddCTP dephosphorylation starts when ATP fall down to values lower than 1 mM.

In conclusion, ddCTP is stable when encapsulated into human erythrocytes. However, a dephosphorylating enzyme is present in these cells but it is usually inhibited by cellular concentrations of ATP.

4) Targeting of ddCTP-loaded erythrocytes to human monocytes/macrophages:

Targeting of erythrocytes to monocytes/macrophages (M/M) can be obtained in a number of ways including the opsonization of these cells with heterologous antibodies. A more sophisticated approach can be the manipulation of the cell in a way that membrane antigenic sites become accessible to autologous immunoglobulins commonly present in the plasma. A number of manipulations are currently available to this end as incubation with phenylhydrazine, melittine, acridine orange, $ZnCl_2$, etc. These agents act by different mechanisms. A procedure as mild as possible is based on an observation that $ZnCl_2$ causes band 3 clustering (band 3 is the predominant transmembrane protein in mammalian erythrocytes and functions as anion transport system) and autologous IgG binding. The band 3 clusters should be make irreversible by treatment with cross-linking agents.

The procedure is as follows:

1. erythrocytes are submitted to the procedure of ddCTP encapsulation as specified above.

2. loaded erythrocytes suspension (10% hematocrit) in 1 mM $ZnCl_2$ are treated with 1 mM BS$^3$ (Bis (sulfosuccinimidyl)suberate) for 15 min, at room temperature, and then washed once in buffer A containing 10 mM ethanolamine and once with buffer A containing 1% (w/v) of BSA. These cells were then used immediately or incubated in autologous plasma for 30–60 min at room temperature for the determination of bound IgG molecules.

The determination of erythrocytes bound autologous IgG was performed by evaluating $^{125}$I-Protein A binding. Briefly, following the procedure of encapsulation the loaded erythrocytes were divided into two aliquots one of which serve as a control while the other was treated with $ZnCl_2$ and $BS^3$ as above. Both erythrocytes fractions were incubated at room temperature in autologous plasma for 30–60 min at an hematocrit of 40%. After this incubation the cells were washed twice in 10 mM HEPES buffer, pH 7.4, containing 140 mM NaCl, 5 mM glucose, 2% (w/v) bovine serum albumin (HEPES buffer). Washed erythrocytes (50 µl) were then resuspended in 100 µl of HEPES buffer containing $5.10^5$ c.p.m. of $^{125}$I-Protein A (1.1 mCi/mg protein A) and incubated at room temperature for 30 min. The erythrocytes were then extensively washed in HEPES buffer (four times) and finally counted in a Beckman 5500 g-counter.

This treatment allowed the binding of 1,500 IgG molecules per cell (30–40 IgG/cell in unloaded or native erythrocyte).

These erythrocytes are actively recognized by human monocytes/macrophages through their Fc and C3b receptors and then occurs phagocytosis of around 1 erythrocyte per monocytes/macrophages, whereas the basal values of phagocytosis (for untreated cells) are of 0.1–0.2 erythrocytes per monocytes/macrophages (see hereafter).

5) Recognition of ddCTP-loaded and unloaded erythrocytes by monocytes/macrophages:

Human monocytes/macrophages were prepared from heparinized blood by Lymphoprep (Nyegaard & Co Oslo, Norway) centrifugation. Mononuclear cells collected at the interface between the Lymphoprep and plasma were washed in 5 mM sodium potassium phosphate buffer, pH 7.4, containing 0.9% (w/v) NaCl, 5 mM glucose and finally resuspended in RPMI 1640 medium containing 10% (v/v) fetal bovine serum (FCS). $8.10^6$ cells were placed into 100 mm Corning dish and incubated overnight at 37° C. and 5% $CO_2$. Adherent monocytes/macrophages cells were separated from the lymphocytes by three washing steps in RPMI/FCS medium, counted by Tripan blue exclusion dye and incubated with ddCTP-loaded erythrocytes treated or not with $ZnCl_2$ plus $BS^3$ or with unloaded erythrocytes overnight at 37° C. at a ratio of 100 erythrocytes per monocytes/macrophages. During the loading procedure $^{125}$I-ubiquitin (2.1 mCi/mg) was also encapsulated as an internal marker to follow phagocytosis both into ddCTP-loaded on ddCTP-unloaded erythrocytes. (Ubiquitin is a polypeptide of 8 KDa that can be easily encapsulated and is retained by the erythrocytes).

After monocytes/macrophages-erythrocytes incubation the dishes were extensively washed with RPMI 1640 medium to remove all erythrocytes not phagocytosed, followed by a 0.9% ammonium chloride washing step to remove adherent erythrocytes that were not yet phagocytosed.

Finally monocytes/macrophages were washed again in RPMI medium and counted in a Beckman 5500 counter. ddCTP-loaded erythrocytes treated with $ZnCl_2$ and $BS^3$ are actively recognized by human monocytes/macrophages and phagocytosed in the proportion of more than one erythrocyte per monocytes/macrophages against basal values of 0.1–0.2 erythrocytes per monocytes/macrophages for the ddCTP-unloaded or ddCTP-loaded erythrocytes not receiving $ZnCl_2$ and $BS^3$.

ddCTP encapsulated into erythrocytes was found in the monocytes/macrophages following the procedure described above suggesting that human erythrocytes can really be used to deliver ddCTP to monocytes/macrophages.

In this case $^{125}$I-ubiquitin was not encapsulated but $^3$H-ddCTP was used instead of the unlabeled drug. monocytes/macrophages after the phagocytosis step were extracted with 10% $HClO_4$ and processed as above for the HPLC separation of nucleotide and nucleotide analogs followed by liquid scintillation counting of the fractions collected at the exit of the HPLC system. The concentration of ddCTP in monocytes/macrophages after phagocytosis was 2.88 µM.

Similar experiments were also performed on mice erythrocytes to do in vivo studies. The results are similar to those reported above. The in vivo half life of these erythrocytes was evaluated by following the radioactivity of $^{125}$I-ubiquitin-loaded erythrocytes coencapsulated with ddCTP in erythrocytes treated or not with $ZnCl_2$ and $BS^3$.

In this case, the radioactivity associated with the erythrocytes was determined on blood collected from the tail vein of animals receiving the erythrocytes described above. The values obtained showed an half-life of 3.5 days for ddCTP-loaded erythrocytes treated with $ZnCl_2$ and $BS^3$ against values of 10.5 days for the ddCTP-loaded erythrocytes not treated with $ZnCl_2$ and $BS^3$.

$ZnCl_2$ concentrations lower than 1 mM provided proportional increasing half-life of the treated erythrocytes (from 3.5 days at 1 mM to 10.5 days at 0.01 mM $ZnCl_2$). The lowest $ZnCl_2$ concentration able to modify red cell survival in mice was 0.1 mM.

The majority of these cells are sequestered into liver and spleen as expected from the organ distribution of cells of the monocyte, macrophage lineage.

6) In vivo inhibition of LP-BM5 infection by the administration of ddCTP-loaded erythrocytes:

Mice infected with LP-BM5 murine leukemia virus develop lymphadenopathy, splenomegaly, hypergammaglobulinemia and immunosuppression. This disease has many features in common with human acquired immunodeficiency syndrome (AIDS).

C57BL/6 mice have been infected with LP-BM5 murine virus obtained from the supernatant of SC-1 chronically infected cells. LP-BM5 is de for instance in Klinken S. P. et al., (1988). Evolution of b cell lineage lymphomas in mice with a retrovirus-induced immunodeficiency syndrome. MAIDS. J. Immunol. 140: 1123–1131.

By this treatment all the animals develop the signs of the disease and are usually killed after 3 months from the infection for spleen examination.

Two groups of five mice were infected with LP-BM5 ($6.6 \times 10^5$ of reverse transcriptase). A third group was used as a control. One infected group received, in addition, $360 \times 10^6$ of erythrocytes (13.5 µl) containing 5 µmol of ddCTP/ml erythrocytes and treated to increase their targeting to monocytes/macrophages at ten day intervals. The first administration of ddCTP-loaded erythrocytes was done 24 h after the infection. Three months later all the animals were killed and examined.

Figure 1:
FIGS. 1 A–1C represents the spleen.

The animals receiving ddCTP-loaded erythrocytes had less splenomegaly (FIG. 1), less lymphadenopathy and reduced amount of immunoglobulin in their serum (Table 1).

TABLE 1

| Number of days following the infection performed on day 0 | Immunoglobulin G concentrations (mg/100 ml) | | | |
|---|---|---|---|---|
| | 35 | 62 | 77 | 84 |
| Experiment One | | | | |
| Control | 77 | 86 | 80 | 105 |
| Infected | 88 | 115 | 230 | 160 |
| Infected-Treated | 80 | 88 | 88 | 120 |
| Experiment Two | | | | |
| Control | 70 | 105 | 105 | 115 |
| Infected | 84 | 480 | 240 | 175 |
| Infected-Treated | 72 | 160 | 130 | 125 |

These results prove that very low amounts of ddCTP-loaded erythrocytes administered at 10 day intervals are effective in reducing the infection ability of LP-BM5 a murine retrovirus that is responsible in mice for a disease similar with human AIDS.

7) In vitro inhibition of HIV production by ddCTP-loaded erythrocytes:

The efficiency of ddCTP-loaded erythrocytes was also examined in vitro on monocytes/macrophages infected cells. Two experiments obtained with macrophages from two different individuals provided similar results.

Monocytes/macrophages were prepared from mononuclear peripheral blood cells obtained by centrifugation on Lymphoprep commercialized by Nyegaard & Co., Oslo, Norway. Adhesion was obtained in the presence of 20% heat inactivated human serum, while monocytes/macrophages (more than 95% pure) were infected by HIV I (LAU Bru isolate) for 8 h at a p24 concentration of 40 ng/$10^7$ monocytes/macrophages cells. p24 is a virus protein described in Reitz M. S. et al., (1987). Human T-cell leukemia viruses. The molecular basis of blood diseases. Stamatoyannopoulos G., Nienhuis A. W., Leder P., Majerns P. W. eds. Saunder Comp. 377–406. Mononuclear cells were then washed and further incubated with ddCTP-loaded erythrocytes (1 µmol/ml erythrocytes) for 20 h.

The non ingested red blood cells were then removed and monocytes/macrophages maintained in RPMI 1640 medium containing 10% FCS for 21 days. Cellular p24, the amount of p24 in the medium and reverse transcriptase in the medium were assayed. The results obtained with the two mentioned experiments are not different of more than 10%, and on FIG. 2, is represented the mean value of these results. These data show that promotion of phagocytosis by the compositions of the invention decrease HIV production. ddCTP-loaded erythrocytes further reduces HIV production confirming the validity of the compositions of the invention, as a new route for ddCTP administration to infected monocytes/macrophages.

We claim:

1. A transformed erythrocyte containing a triphosphorylated nucleoside analog selected from the group consisting of 2',3'-dideoxycytidine-5'-triphosphate (ddCTP) and 3'-azido-3'-deoxythymidine-5'-triphosphate (AZT-TP) which does not naturally occur in humans or animals, wherein said triphosphorylated nucleoside analog is substantially free of degradation products and inhibits reverse transcriptase.

2. A transformed erythrocyte of claim 1 further comprising ATP incorporated therein.

3. A transformed erythrocyte of claim 2 wherein the concentration of ATP is 1 to 3 mM.

4. A method of treating viral infections in warm-blooded animals comprising administering to warm-blooded animals an antivirally effective amount of the transformed erythrocyte of claim 3.

5. A transformed erythrocyte of claim 1 wherein at least one surface protein or transmembrane protein of said erythrocyte is cross-linked following treatment with a clustering agent and a protein cross-linking agent.

6. A transformed erythrocyte of claim 5 wherein the clustering agent is $ZnCl_2$ and the crosslinking agent is bis(sulfosuccinimidyl)-suberate.

7. An antiviral composition comprising an antivirally effective amount of the transformed erythrocyte of claim 1 and a pharmaceutically acceptable carrier.

8. A composition of claim 7 wherein the total volume is 1 to 10 mls and the total concentration of triphosphorylated compound is 1 to 10 mM.

9. A process for the preparation of the transformed erythrocyte of claim 1 comprising (a) lysing the membrane of said erythrocyte by dialysis of an aqueous suspension of erythrocytes against an aqueous solution that is hypotonic with respect to the suspension;

(b) adding the triphosphorylated compound;

(c) increasing the osmotic pressure of the resulting erythrocyte lysate mixture with a solution hypertonic to the lysate mixture whereby the erythrocyte membranes are resealed; and (d) washing the resealed erythrocytes.

10. The process of claim 9 wherein ATP is added with the triphosphorylated compound to the erythrocyte lysate.

11. A method of treating viral infections in warm-blooded animals comprising administering to warm-blooded animals an antivirally effective amount of the transformed erythrocyte of claim 1.

* * * * *